United States Patent

Stroot

[11] 4,045,826
[45] Sept. 6, 1977

[54] GLENOID COMPONENT FOR SHOULDER PROSTHESIS

[76] Inventor: Jerome H. Stroot, 2645 Ocean Ave., San Francisco, Calif. 94132

[21] Appl. No.: 766,878

[22] Filed: Feb. 9, 1977

[51] Int. Cl.² .............................................. A61F 1/24
[52] U.S. Cl. ...................................... 3/1.91; 128/92 C
[58] Field of Search ................................ 3/1.9–1.913, 3/1; 128/92 C, 92 CA

[56] References Cited

U.S. PATENT DOCUMENTS

| | | | |
|---|---|---|---|
| 3,528,109 | 9/1970 | Scales | 3/1.91 |
| 3,694,820 | 10/1972 | Scales et al. | 3/1.91 |
| 3,842,442 | 10/1974 | Kolbel | 3/1.91 |

*Primary Examiner*—Ronald L. Frinks
*Attorney, Agent, or Firm*—Robert G. Slick

[57] ABSTRACT

A glenoid component for a shoulder prosthesis is provided which is symmetrical so that it can be used as a replacement for either shoulder. The glenoid component is designed in such a way that it is strong yet it requires the removal of a minimum amount of bone.

1 Claim, 9 Drawing Figures

U.S. Patent  Sept. 6, 1977  Sheet 1 of 2  4,045,826
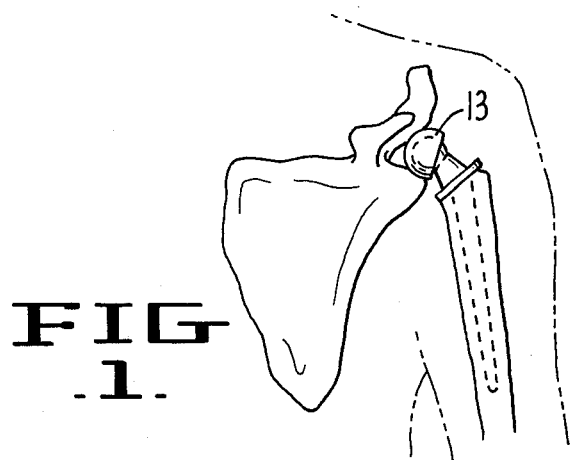
FIG. 1.
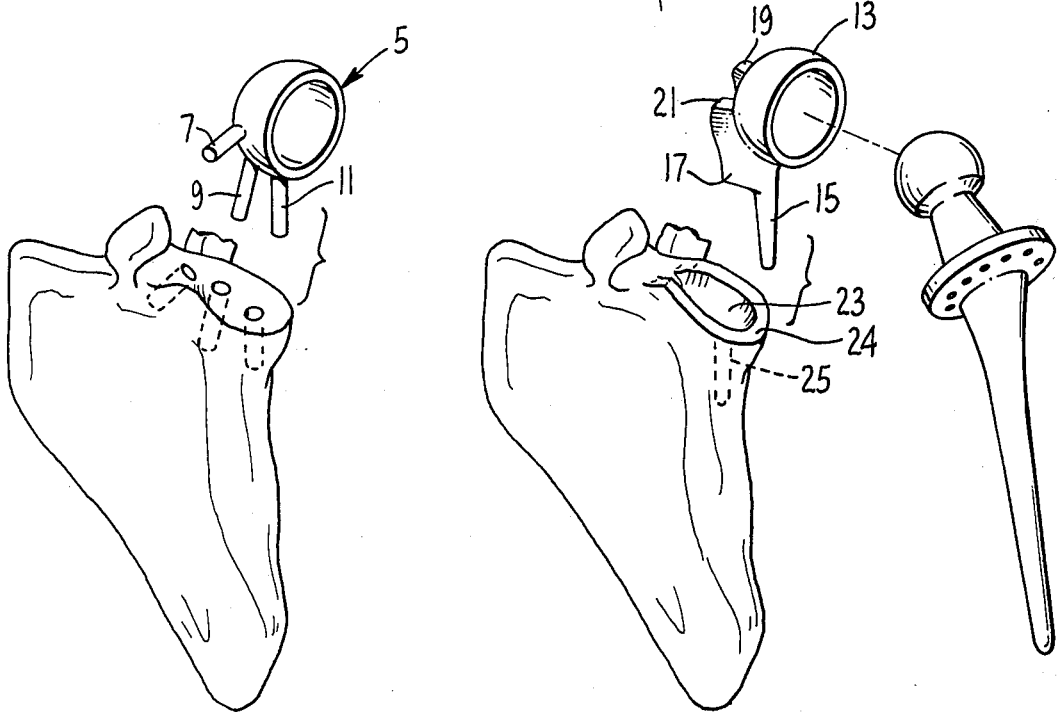
FIG. 2.
PRIOR ART
FIG. 4.
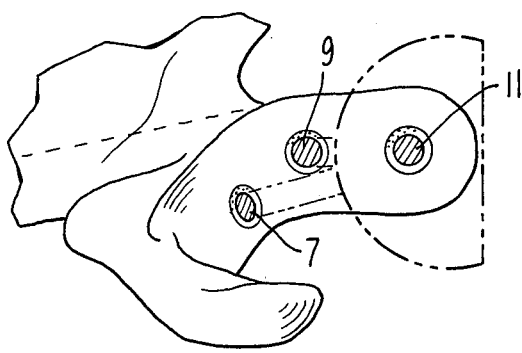
FIG. 3.
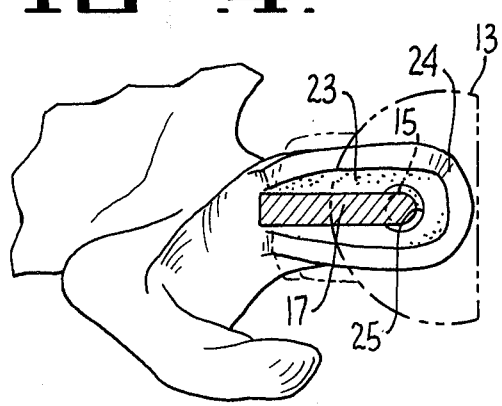
FIG. 5.

GLENOID COMPONENT FOR SHOULDER PROSTHESIS

SUMMARY OF THE INVENTION

In substantially all of the shoulder prosthesis heretofore known, the prosthesis is designed with a plurality of attachment spines or pins which of necessity must be of a different configuration for the right shoulder than for the left. Thus, it is necessary for a surgical supply house and hospitals to stock glenoid components for the right shoulder and for the left shoulder.

Another disadvantage of prior art is the problem of removal of the component in the event trouble is encountered and it must be replaced with another prosthesis later in life. The plurality of pins (spines) of the prior art necessitates the removal of substantial amounts of bone, making it more difficult for a successful replacement.

The prosthesis of the present invention requires a minimum amount of bone surgery for insertion, is intrinsically strong and still is adequately fixed to bone with the filler cement. It is relatively easy to replace if this should ever become necessary.

Although the glenoid component of the present invention is particularly adapted for use with the humerus component disclosed and claimed in my patent application Ser. No. 653,277 filed Jan. 28, 1976, its use is not limited to this type of humerus component and may be used with any humerus component. Thus, by suitably proportioning the size of the cup and radius of curvature, the novel glenoid component of the present invention could be used to provide a prosthesis having a wandering fulcrum as set forth in my prior U.S. Pat. No. 3,979,778.

Various other objects and features of the invention will be brought out in the balance of the specification.

BRIEF DESCRIPTION OF THE DRAWINGS

In the drawings forming part of this application:

FIG. 1 is a front view of a prosthesis including the novel glenoid component of the present invention.

FIG. 2 is an exploded view of a popular type of prior art prosthesis.

FIG. 3 is a section through the shoulder of the prosthesis of FIG. 2.

FIG. 4 is an exploded view of the prosthesis of the present invention and the shoulder prepared to receive the novel glenoid component.

FIG. 5 is a top plan view, partly in section, of the glenoid component showing its installation in the shoulder.

DESCRIPTION OF THE PREFERRED EMBODIMENTS

Figure 6:
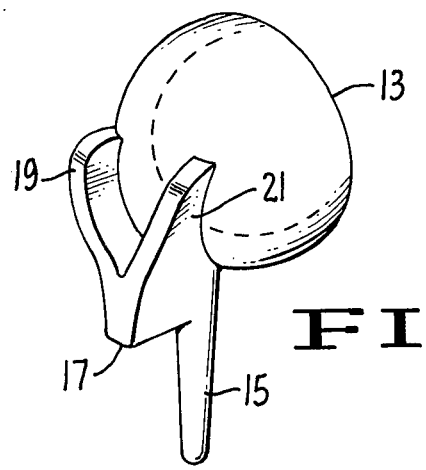
FIG. 6 is a perspective view of the glenoid component of the present invention.
Figure 7:
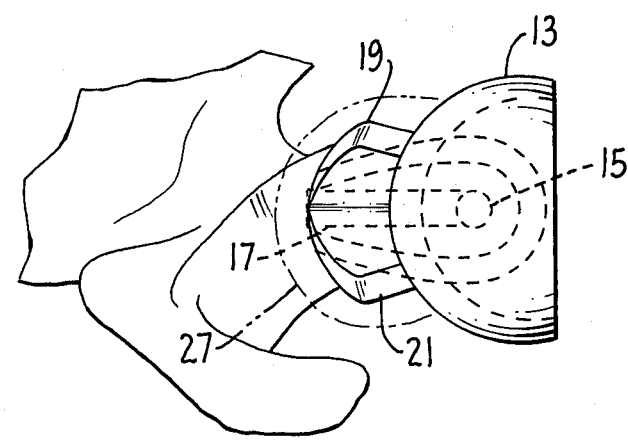
FIG. 7 is a section, similar to the section in FIG. 3, showing the symmetrical implantment of the present invention.

Referring now to the drawings by reference characters, FIGS. 2 and 3 illustrate a popular type of prior art prosthesis having a hemispherical cup generally designated 5 and having pins 7, 9 and 11 attached to the outer surface thereof. As can best be seen in FIG. 3, the placement of these pins is not symmetrical so that it is necessary to provide separate glenoid components for the two shoulders. These pins are cemented in place and it is readily apparent that because of the divergent nature of the pins a very substantial amount of the natural glenoid must be removed in order to replace the glenoid component should it be necessary at some future date.

The novel glenoid component of the present invention consists of a hemispherical cup 13 having a single pin 15 extending downwardly from near the bottom of the outer surface of the hemisphere. In addition a fin 17 extends from the base of the pin 15 on its medial aspect and extends upwardly in a circumferential direction until it bifurcates into two fins 19 and 21 which diverge to form reinforcing ribs strengthening the prosthesis as well as enhancing its fixation to bone by means of the cement. The shape of the prosthesis and location of the fins allow the anterior and posterior rim of the natural glenoid to remain intact.

Figure 9:
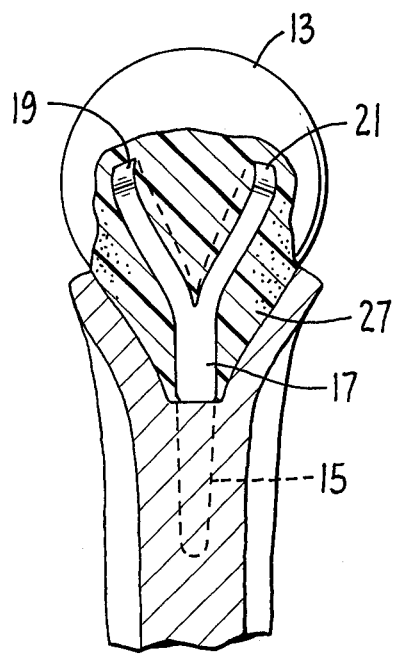
FIG. 9 is a side view of the glenoid component of the present invention.
Figure 8:
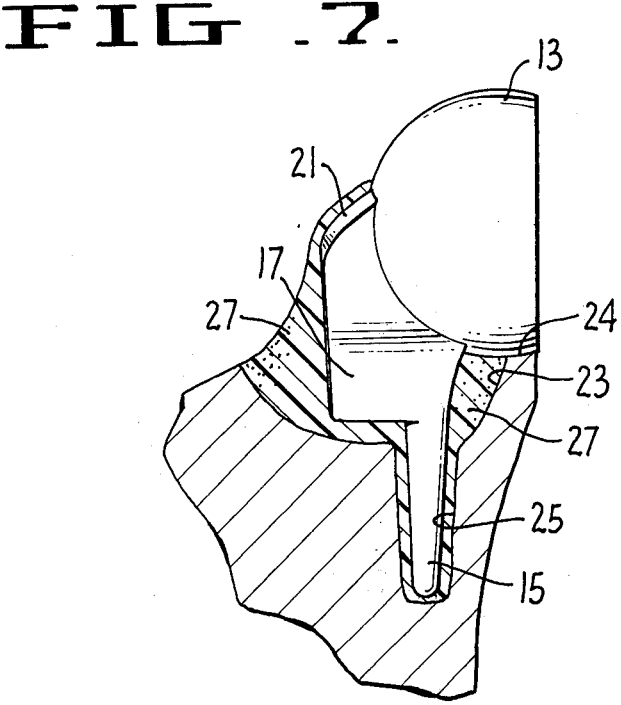
FIG. 8 is a front view of the glenoid component of the present invention.

To use the component of the present invention, the natural glenoid is excavated, leaving the view intact except for perhaps the very superior portions which may have to be sacrificed to receive the fin of the glenoid prosthesis. A slot 23 is made in the glenoid leaving a rim 24. At the base of the slot a hole 25 is made extending toward the inferior end of the scapula along its axillary border. As is best seen in FIGS. 8 and 9 one now places the novel glenoid component into the hole 25 and the fin extending into slot 23. These are cemented in place as is shown at 27 utilizing the technique well known to those skilled in the art. The reinforcing members 19 and 21 lie between the spine of the acromion and the coracoid process but are not directly attached thereto.

I claim:

1. A glenoid component for a shoulder prosthesis comprising:
   a. a hemispherical cup;
   b. a pin extending outwardly from the outer surface of said cup;
   c. a wedge-shaped member extending at right angles to said pin;
   d. a pair of reinforcing ribs extending upwardly from the pin and the wedge and being attached to the outer surface of the hemispherical cup;
   e. providing a symmetrical glenoid component adapted to be used in either shoulder.

* * * * *